(12) United States Patent
Kay et al.

(10) Patent No.: US 8,124,407 B2
(45) Date of Patent: *Feb. 28, 2012

(54) CIRCULAR NUCLEIC ACID VECTORS, AND METHODS FOR MAKING AND USING THE SAME

(75) Inventors: Mark A. Kay, Los Altos, CA (US); Zhi-Ying Chen, Foster City, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/006,356

(22) Filed: Jan. 13, 2011

(65) Prior Publication Data

US 2011/0126306 A1    May 26, 2011

Related U.S. Application Data

(63) Continuation of application No. 10/652,729, filed on Aug. 28, 2003, now Pat. No. 7,897,380.

(60) Provisional application No. 60/463,672, filed on Apr. 16, 2003, provisional application No. 60/407,344, filed on Aug. 29, 2002.

(51) Int. Cl.
*C12N 15/00* (2006.01)

(52) U.S. Cl. ............... 435/320.1; 435/69.1; 435/252.33; 435/235.1

(58) Field of Classification Search ..................... None
See application file for complete search history.

(56) References Cited

U.S. PATENT DOCUMENTS

| | | |
|---|---|---|
| 5,922,687 A | 7/1999 | Mann et al. |
| 5,985,847 A | 11/1999 | Carson et al. |
| 6,143,530 A | 11/2000 | Crouzet et al. |
| 6,387,670 B1 | 5/2002 | Leblois-Prehaud et al. |
| 6,492,164 B1 | 12/2002 | Crouzet et al. |
| 6,514,757 B1 | 2/2003 | Ball et al. |
| 6,562,800 B1 | 5/2003 | McMillan |
| 6,632,672 B2 | 10/2003 | Calos |
| 6,696,278 B1 | 2/2004 | Carstens |
| 2003/0032092 A1 | 2/2003 | Blanche et al. |
| 2004/0214329 A1 | 10/2004 | Kay et al. |
| 2006/0211117 A1 | 9/2006 | Bigger et al. |

FOREIGN PATENT DOCUMENTS

| | | |
|---|---|---|
| CA | 2211427 | 8/1996 |
| CA | 2358263 | 10/2002 |
| EP | 1035208 | 9/2000 |
| EP | 0815214 | 7/2007 |
| WO | 94/09127 | 4/1994 |
| WO | 98/22607 | 11/1997 |
| WO | 02/083889 | 10/2002 |

OTHER PUBLICATIONS

Thomason et al., vol. 265 (2001) pp. 1031-1038.*

Ascadi et al. "Direct Gene Transfer and Expression into Rat Heart In Vivo" New Biol. (1991) 3:71-81.

Bigger; et al., "An araC-controlled Bacterial cre Expression System to Produce DNA Minicircle Vectors for Nuclear and Mitochondrial Gene Therapy", J. Biol. Chem. (2001), 23018-27.

Brough; et al., "Activation of Transgene Expression by Early Region 4 is Responsible for a High Level of Persistent Transgene Expression from Adenovirus Vectors In Vivo", Journal of Virology (1997), 71(12):9206-9213.

Chen; et al., "Improved Production and Purification of Minicircle DNA Vector Free of Plasmid Bacteria Sequences and Capable of Persistent Transgene Expression In Vivo", Human Gene Therapy (2005), 16(1):126-131.

Chen; et al., "Silencing of episomal transgene expression by plasmid bacterial DNA elements in vivo", Gene Therapy (2004), 11(10):856-864.

Chen; et al., "Minicircle DNA Vectors Devoid of Bacterial DNA Result in Persistent and High-Level Transgene Expresssion in Vivo", Molecular Therapy (2003), 8(3):495-500.

Darquet; et al., "Minicricle: an improved DNA molecule for in vitro and in vivo gene transfer", Gene Therapy (1999), 6:209-18.

Fletcher; et al., "Fine-Structure Deletion Analysis of the Transcriptional Silencer of the proU Operon of *Salmonella typhimurium*", J. Bact. (1995), 177:4508-13.

Gao; et al., "Delivery of a retroviral vector expressing human beta-glucuronidase to the liver and spleen decreases lysosomal storage in mucopolysaccharidosis VII mice", Mol. Ther. (2000), 2(3):233-44.

Groth; et al., "A phage integrase directs efficient site-specific integration in human cells", PNAS (2000), 97 (11):5995-6000.

Hickman; et al. "Gene Expression Following Direct Injection of DNA into Liver" Human Gene Therapy (1994), 5:1477-1483.

Jordi; et al., "The Downstream Regulatory Element of the proU Operon of *Salmonella typhimurium* Inhibits Open Complex Formation by RNA Polymerase at a Distance", J. Biol. Chem. (2000), 275:21123-28.

(Continued)

*Primary Examiner* — Jim Ketter
(74) *Attorney, Agent, or Firm* — Bozicevic, Field & Francis LLP; Bret E. Field; Elizabeth A. Alcamo

(57) ABSTRACT

Circular nucleic acid vectors that provide for persistently high levels of protein expression are provided. The circular vectors of the subject invention are characterized by being devoid of expression-silencing bacterial sequences, where in many embodiments the subject vectors include a unidirectional site-specific recombination product hybrid sequence in addition to an expression cassette. Also provided are methods of using the subject vectors for introduction of a nucleic acid, e.g., an expression cassette, into a target cell, as well as preparations for use in practicing such methods. The subject methods and compositions find use in a variety of different applications, including both research and therapeutic applications. Also provided is a highly efficient and readily scalable method for producing the vectors employed in the subject methods, as well as reagents and kits/systems for practicing the same.

21 Claims, 4 Drawing Sheets

OTHER PUBLICATIONS

Keravala; et al., "A diversity of serine phage integrases mediate site-specific recombination in mammalian cells", Mol. Gen. Genomics (2006), 275:135-146.

Miao; et al. "Inclusion of the Hepatic Locus Control Region, an Intron, and Untranslated Region Increases and Stabilizes Hepatic Factor IX Gene Expression in Vivo but Not in Vitro" Molecular Therapy (2000), 1(6):522-532.

Miao; et al., "Long-Term and Therapeutic-Level Hepatic Gene Expression of Human Factor IX after Naked Plasmid Transfer in Vivo", Molecular Therapy (2001), 3(6):947-957.

Nakai; et al. "Extrachromosomal Recombinant Adeno-Associated Virus Vector Genomes Are Primarily Responsible for Stable Liver Transduction In Vivo" Journal of Virology(2001), p. 6969-6976.

Nakai; et al. "Persistant hF.IX Expression in Mouse Hepatocytes From Episomal rAAV Circular Intermediates does not rely on the presence of AAV-*ITR but the Structure of Expression Cassette Itself" Blood (2000), 96(11 Part 1):431A print.

Schnetz; et al., "Silencing of the *Escherichia coli* bgl promoter: effects of template supercoiling and cell extracts on promoter activity in vitro", Nuc. Acids Res. (1996), 24:2422-28.

Thorpe; et al., "In vitro site-specific integration of bacteriophage DNA catalyzed by a recombinase of the resolvase/invertase family", PNAS (1998), 95:5505-5510.

Wolff; et al "Direct Gene Transfer into Mouse Muscle In Vivo" Science(1990), 247:1465-1468.

Yant; et al. "Somatic Integration and Long-Term Transgene Expression in Normal and Haemophilic Mice Using a DNA Transposon System" Nature Genetics(2000), 25:35-41.

Yu; et al., "Characterization of the Binding Sites of Two Proteins Involed in the Bacteriophage P2 Site-Specific Recombination System", J. Bacter. (1993), 175:1239-49.

* cited by examiner

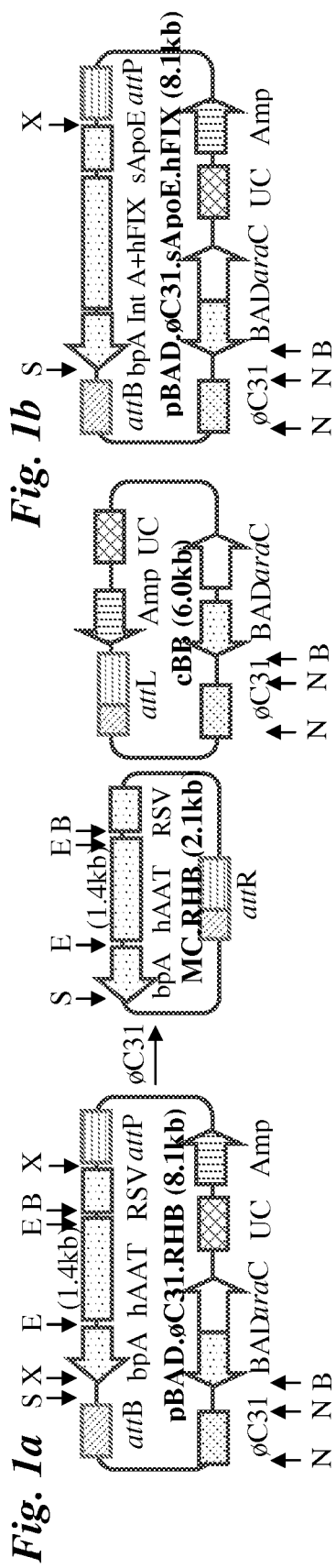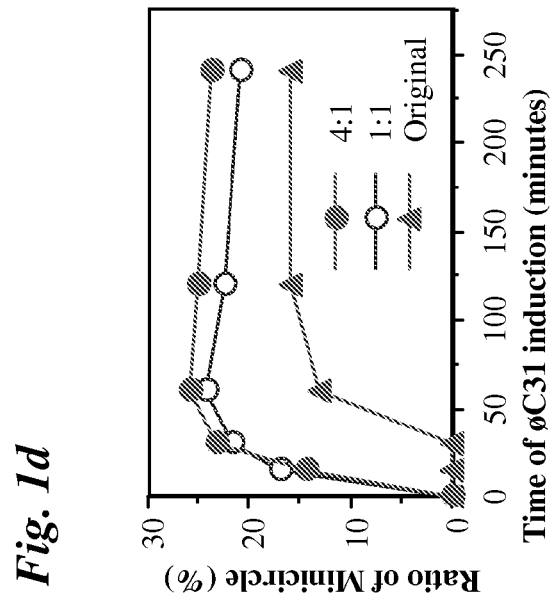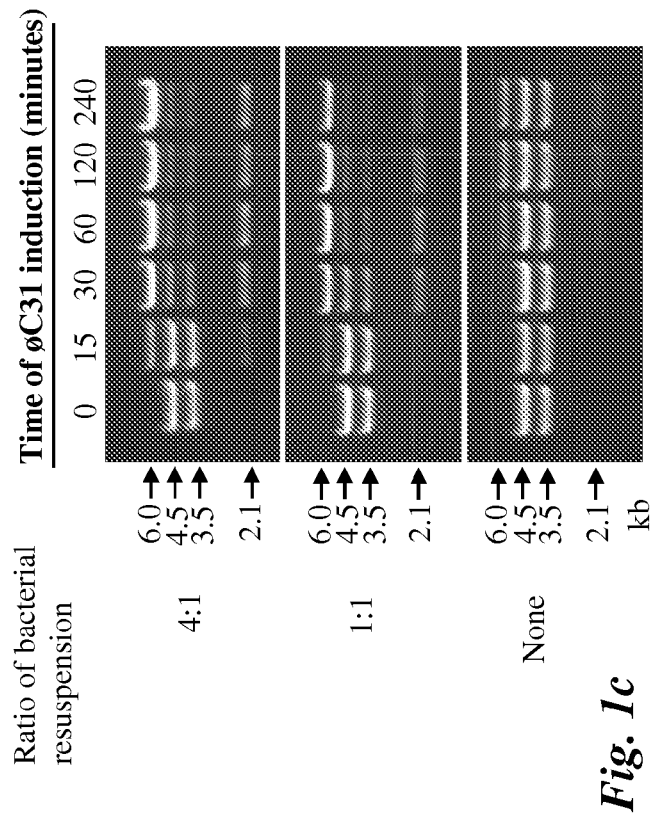
Fig. 1a, Fig. 1b, Fig. 1c, Fig. 1d

CIRCULAR NUCLEIC ACID VECTORS, AND METHODS FOR MAKING AND USING THE SAME

CROSS-REFERENCE TO RELATED APPLICATIONS

This application is a continuation application of U.S. patent application Ser. No. 10/652,729 filed on Aug. 28, 2003; which application claims priority (pursuant to 35 U.S.C. §119 (e)) to the filing date of the U.S. Provisional Patent Application Ser. No. 60/407,344 filed Aug. 29, 2002 and U.S. Provisional Patent Application Ser. No. 60/463,672 filed Apr. 16, 2003; the disclosures of which are herein incorporated by reference.

GOVERNMENT RIGHTS

This invention was made with government support under federal grant nos. HL64274 awarded by The National Institutes of Health. The United States Government has certain rights in this invention.

INTRODUCTION

1. Field of the Invention

The field of this invention is molecular biology, particularly transformation and specifically vectors employed in transformation.

2. Background of the Invention

The introduction of an exogenous nucleic acid sequence (e.g., DNA) into a cell, a process known as "transformation," plays a major role in a variety of biotechnology and related applications, including research, synthetic and therapeutic applications. Research applications in which transformation plays a critical role include the production of transgenic cells and animals. Synthetic applications in which transformation plays a critical role include the production of peptides and proteins, as well as therapeutic RNAs, such as interference RNA or ribozymes. Therapeutic applications in which transformation plays a key role include gene therapy applications. Because of the prevalent role transformation plays in the above and other applications, a variety of different transformation protocols have been developed.

In many transformation applications, it is desirable to introduce the exogenous DNA in a manner such that it provides for long-term expression of the protein encoded by the exogenous DNA. Long-term expression of exogenous DNA is primarily achieved through incorporation of the exogenous DNA into a target cell's genome. One means of providing for genome integration is to employ a vector that is capable of homologous recombination. Techniques that rely on homologous recombination can be disadvantageous in that the necessary homologies may not always exist; the recombination events may be slow; etc. As such, homologous recombination based protocols are not entirely satisfactory.

Accordingly, alternative viral based transformation protocols have been developed, in which a viral vector is employed to introduce exogenous DNA into a cell and then subsequently integrate the introduced DNA into the target cell's genome. Viral based vectors finding use include retroviral vectors, e.g., Moloney murine leukemia viral based vectors. Other viral based vectors that find use include adenovirus derived vectors, HSV derived vectors, sindbis derived vectors, etc. While viral vectors provide for a number of advantages, their use is not optimal in many situations. Disadvantages associated with viral based vectors include immunogenicity, viral based complications, as well as integration mediated mutation problems, and the like.

Therefore, there is continued interest in the development of additional methods of transforming cells with exogenous nucleic acids to provide for persistent, long-term expression of an encoded protein. Of particular interest is the development of a non-viral in vivo nucleic acid transfer protocol and vector that provides for persistent protein expression without concomitant genome integration, where the vector provides for persistent expression in a manner that is independent of the sequence and direction of the of the expression cassette present on the vector.

3. Relevant Literature

U.S. patents of interest include 5,985,847 and 5,922,687. Also of interest is WO/11092. Additional references of interest include: Wolff et al., "Direct Gene Transfer Into Mouse Muscle In Vivo," Science (March 1990) 247: 1465-1468; Hickman et al., "Gene Expression Following Direct Injection of DNA Into Liver," Hum. Gen. Ther. (December 1994) 5:1477-1483; and Acsadi et al., "Direct Gene Transfer and Expression Into Rat Heart In Vivo," New Biol. (January 1991) 3:71-81.

SUMMARY OF THE INVENTION

Circular nucleic acid vectors that provide for persistently high levels of protein expression are provided. The circular vectors of the subject invention are characterized by being devoid of expression-silencing bacterial sequences, where in many embodiments the subject vectors include a unidirectional site-specific recombination product sequence in addition to an expression cassette. Also provided are methods of using the subject vectors for introduction of a nucleic acid, e.g., an expression cassette, into a target cell, as well as preparations for use in practicing such methods. The subject methods and compositions find use in a variety of different applications, including both research and therapeutic applications. In addition, methods for making such vectors, as well as reagents and kits/systems for practicing is the same, are also provided.

BRIEF DESCRIPTION OF THE DRAWINGS

FIGS. 1a to 1d. øC31-mediated production of minicircle in E. coli. FIG. 1a, Flow chart of øC31 integrase-mediated intramolecular recombination of pBADøC31.RHB and resulting DNA products cBB and MC.RHB. RSV, Rous Sarcoma virus long terminal repeat promoter; hAAT, human α1-antitrypsin; bpA, bovine growth factor polyadenylation signal; RHB, RSV.hAAT.bpA expression cassette; Amp, ampicillin resistant gene; BAD, araBAD promoter; araC, araC repressor; attB, bacterial attachment site; attP, phage attahment site; attL, left hybrid sequence; attR, right hybrid sequence; UC, pUC origin of DNA replication. MC, minicircle; cBB, circular bacterial backbone. Restriction sites: B, BamH1, N, Nco I; S, Spe I; and X, Xho I. FIG. 1b, The vector pBAD.øC31.hFIX used for production of minicircle expressing human factor IX (hFIX). sApoE, the artificial enhancer/promoter sApoE.HCR.hAAT[17]; Int A, Intron A. FIG. 1c, Kinetic analysis of L-arabinose-induced øC31-mediated formation of MC.RHB. The influence of different bacteria broth conditions on MC.RHB production was determined. Re-suspension: 4:1 and 1:1, represents the volume of overnight bacterial growth versus volume of fresh LB broth containing 1% L-(+)-arabinose used to resuspend the bacteria; None: 1% L-(+)-arabinose was added directly to the overnight bacterial growth. Bacterial plasmid DNA was isolated from growth media and purified. Each lane loaded with 1 μg of BamH1 digested DNA. The 2.1, and 6.0 kb bands represented the linear MC.RHB, and cBB, respectively, while the 4.5 and 3.5 kb bands were derived from the un-recombined pBAD.øC31,RHB. FIG. 1d, Determination of the time course of minicircle formation by quantification of DNA bands in the gel of FIG. 1c. The values of minicircle ratio are presented as the percent of the 2.1 kb linear minicircle band compared to the combination of all 4 bands in each lane.

is FIGS. 2a to 2b. Trangene expression profiles.

FIG. 3a, Quantification of vector DNA in mouse livers. 20.0 μg of liver DNA was digested with EcoR1 to release the 1.4 kb hAAT cDNA (FIG. 1a, and 2a) and quantified by PhosphaImager. FIG. 3b, Molecular structure of vector DNA in mouse livers. Twenty μg of liver DNA was digested with Bgl II (does not cut in the vector), or Hind III (cuts once in the vector), and vector expression cassette DNA bands visualized after hybridization with a radio-labeled hAAT cDNA probe.

FIG. 5 provides a representation of a gel that demonstrates the purity of a minicricle preparation produced by the protocol of FIGS. 4a to 4c.

DESCRIPTION OF THE SPECIFIC EMBODIMENTS

Figures 2A, 2B:
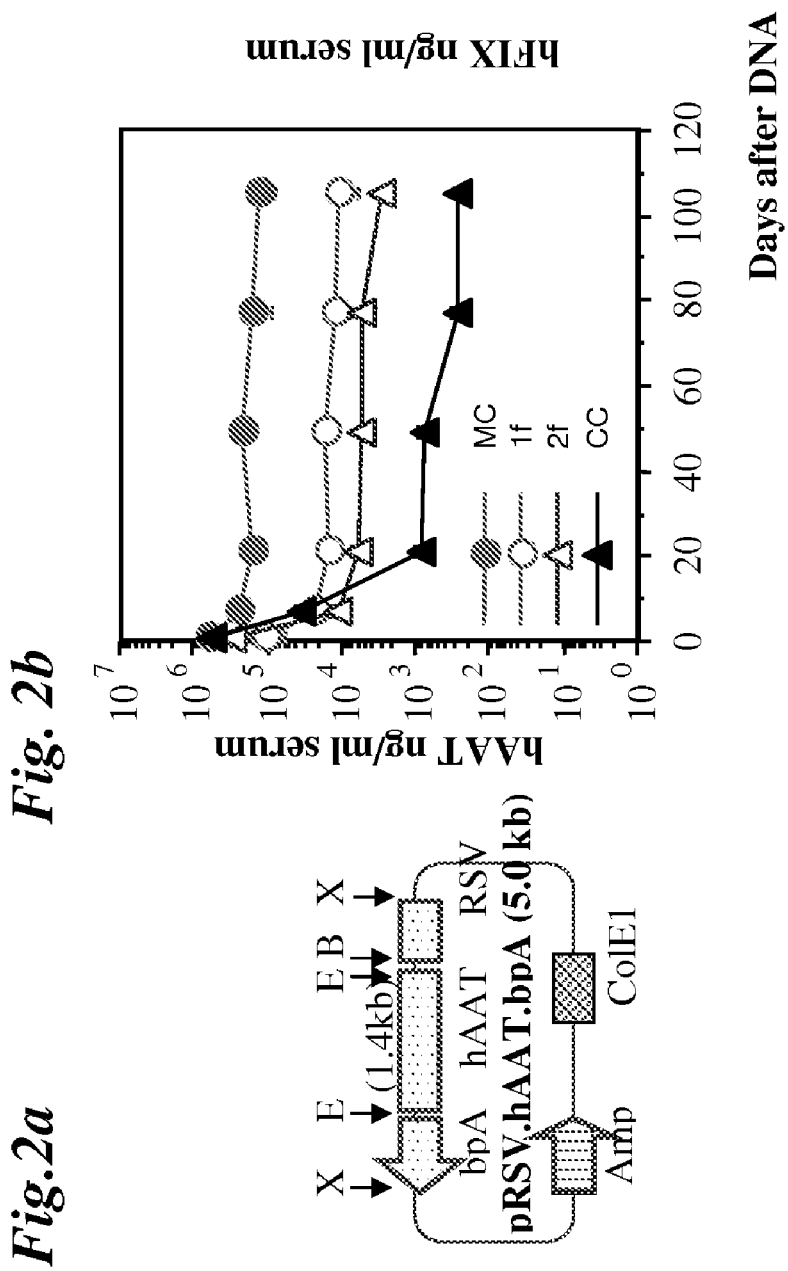
FIG. 2a, The vector pRSV.hAAT.bpA used for preparing the 3 different forms of DNA.
FIG. 2b, Serum hAAT and hFIX expression. Left panel, serum hAAT from mice that received 20.0 μg of closed circular pRSV.hAAT.bpA (CC), or equivalent molar amounts of purified expression cassette (1f, 8.2 μg), 2-fragment DNA (2f, 20.0 μg), or minicircle DNA (MC, 8.5 μg). Right panel, serum hFIX from mice that received 40.0 μg of—unrecombined plasmid—pBAD.øC31.hFIX (FIG. 1b) or equal molar amount of minicircle (16.2 μg).

Circular nucleic acid vectors that provide for persistently high levels of protein expression are provided. The circular vectors of the subject invention are characterized by being devoid of expression-silencing bacterial sequences, where in many embodiments the subject vectors include a unidirectional site-specific recombination product sequence in addition to an expression cassette. Also provided are methods of using the subject vectors for introduction of a nucleic acid, e.g., an expression cassette, into a target cell, as well as preparations for use in practicing such methods. The subject methods and compositions find use in a variety of different applications, including both research and therapeutic applications. In addition, methods for making such vectors, as well as reagents and kits/systems for practicing the same, are also provided.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, methodologies and other invention components that are described in the publications which might be used in connection with the presently described invention.
Methods In the broadest sense, the present invention provides methods of introducing an exogenous nucleic acid into at least one cell, i.e., a target cell. The target cell may be an individual cell, e.g., as may be present in an in vitro environment, or present in a multicellular organism. As such, the subject methods may be in vivo methods, by which is meant that the exogenous nucleic acid is administered directly to the multicellular organism, or in vitro methods, in which the target cell or cells are removed from the multicellular organism and then contacted with the exogenous nucleic acid.

In certain embodiments, the present invention provides methods of introducing an exogenous nucleic acid into a plurality of the cells of a multicellular organism, i.e., a host, where by "plurality" is often meant at least about 0.1 number %, usually at least about 0.5 number % in certain embodiments.

As specified below, in many in vitro embodiments the subject methods rely on systemic administration of the vector employed in the subject methods, where by systemic administration is meant that the vector is administered to the host in a manner such that it comes into contact with more than just a local area or region of the host, where by local area or region of the host is meant a region that is less than about 10%, usually less than about 5% of the total mass of the host. In other in vitro embodiments, local administration protocols are employed. While in the broadest sense the subject methods are methods of introducing any nucleic acid into a host, generally, the exogenous nucleic acid is an expression cassette that encodes a product, e.g., protein, of interest, as described in greater detail infra.
Minicircle Vector A feature of the subject invention is that the methods employ a minimal circular vector, i.e., a minicircle, to deliver the exogenous nucleic acid, hereinafter referred to as "expression cassette" for convenience, to the target cell or cells. The minicircle vector employed in the subject methods is a double-stranded circular DNA molecule. The sequence of the minicircle vector employed in the subject methods is such that it provides for persistent, high level expression of an expression cassette encoded protein present on the vector in a manner that is at least substantially expression cassette sequence and direction independent.

As summarized directly above, a feature of the subject minicircle vectors is that they provide for persistent expression of the expression cassette encoded protein present thereon, as opposed to transient or short-lived expression. By persistent expression is meant that the expression of encoded product, e.g., protein, is at a detectable level that persists for an extended period of time, if not indefinitely, following administration of the subject vector. By extended period of time is meant at least 1 week, usually at least 2 months and more usually at least 6 months. By detectable level is meant that the expression of the encoded product is at a level such that one can detect the encoded product in target cell, or the mammal comprising the same, e.g., in the serum of the mammal, at a therapeutic concentration. See e.g., the experimental section, supra. As compared to a control in which the pBluescript plasmid vector (Stratagene Corporation, La Jolla, Calif.) is employed, protein expression persists for a period of time at a detectable level that is at least about 2 fold, usually at least about 5 fold and more usually at least about 10 fold longer following the subject methods as compared to a control. An encoded product is considered to be at a detectable level if it can be detected using technology and protocols readily available and well known to those of skill in the art. The experimental section infra provides representative detectable levels of the human factor IX protein in mouse serum.

Typically, the above-described persistent expression is not only at a detectable level, but at a high level. A minimal vector is considered to provide for a high level of expression if, after a period of time following its administration, e.g., at least about 28 days, the protein encoded by the expression cassette of the vector is present at high levels in the host, e.g., in the target cells, in the serum of the host, etc. Levels of an encoded product are considered "high" for purposes of the present application if they are present in amounts such that they exhibit detectable activity (e.g., have an impact on the phenotype), e.g., therapeutic activity, in the host. Whether or not the expression level of a particular product is high will necessarily vary depending on the nature of the particular product, but can readily be determined by those of skill in the art, e.g., by an evaluation of whether expression of the product is sufficient to exhibit a desired effect on the phenotype of the host, such as an amelioration of a disease symptom, e.g., reducing clotting time, etc. A minicircle vector according to the subject invention can be tested to see if it provides for the requisite high level of protein is expression by administering it to a host according to the protocols described, infra, and testing for the desired expression level, e.g., in the blood or serum where the expression protein is secreted from the target cell where it is produced, in a tissue lysate of the target cells for non-secreted proteins, and the like.

The minicircle vectors employed in the subject methods include several elements that provide for their utility in the subject methods. The subject minicircle vectors include at least one restriction endonuclease recognized site, i.e., a restriction site, which typically serves as a cloning site, i.e., a site into which nucleic acid may be inserted. A variety of restriction sites are known in the art and may be included in the vector, where such sites include those recognized by the following restriction enzymes: HindIII, PstI, SalI, AccI, HincII, XbaI, BamHI, SmaI, XmaI, KpnI, SacI, EcoRI, and the like. In many embodiments, the vector includes a polylinker (also known in the art as a multiple cloning site), i.e., a closely arranged series or array of sites recognized by a plurality of different restriction enzymes, such as those listed above. As such, in many embodiments, the vectors include a multiple cloning site made up of a plurality of restriction sites. The number of restriction sites in the multiple cloning site may vary, ranging anywhere from 2 to 15 or more, usually 2 to 10.

When employed, the minicircle vectors typically include at least one nucleic acid of interest, i.e., a nucleic acid that is to be introduced into the target cell, e.g., to be expressed as protein in the target cell, etc., as described in greater detail below, where the nucleic acid is typically present as an expression cassette. The subject vectors may include a wide variety of nucleic acids, where the nucleic acids may include a sequence of bases that is endogenous and/or exogenous to the target cell/multicellular organism, where an exogenous sequence is one that is not present in the target cell while an endogenous sequence is one that pre-exists in the target cell prior to introduction. In any event, the nucleic acid of the vector is exogenous to the target cell, since it originates at a source other than the target cell and is introduced into the cell by the subject methods, as described infra. The nature of the nucleic acid will vary depending the particular protocol being performed. For example, in research applications the exogenous nucleic acid may be a novel gene whose protein product is not well characterized. In such applications, the vector is employed to stably introduce the gene into the target cell and observe changes in the cell phenotype in order to characterize the gene. Alternatively, in protein synthesis applications, the exogenous nucleic acid encodes a protein of interest which is to be produced by the cell. In yet other embodiments where the vector is employed, e.g., in gene therapy, the exogenous nucleic acid is a gene having therapeutic activity, i.e., a gene that encodes a product of therapeutic utility.

A variety of different features may be present in the vector. In many embodiments, the vector is characterized by the presence of at least one transcriptionally active gene. By transcriptionally active gene is meant a coding sequence that is capable of being expressed under intracellular conditions, e.g., a coding sequence in combination with any requisite expression regulatory elements that are required for expression in the intracellular environment of the target cell into which the vector is introduced by the subject methods. As such, the transcriptionally active genes of the subject vectors typically include a stretch of nucleotides or domain, i.e., expression module or expression cassette, that includes a coding sequence of nucleotides in operational combination, i.e. operably linked, with requisite transcriptional mediation or regulatory element(s). Requisite transcriptional mediation elements that may be present in the expression module include promoters, enhancers, termination and polyadenylation signal elements, splicing signal elements, and the like.

Preferably, the expression module or expression cassette includes to transcription regulatory elements that provide for expression of the gene in a broad host range. A variety of such combinations are known, where specific transcription regulatory elements include: SV40 elements, as described in Dijkema et al., EMBO J. (1985) 4:761; transcription regulatory elements derived from the LTR of the Rous sarcoma virus, as described in Gorman et al., Proc. Nat'l Acad. Sci. USA (1982) 79:6777; transcription regulatory elements derived from the LTR of human cytomegalovirus (CMV), as described in Boshart et al., Cell (1985) 41:521; hsp70 promoters, (Levy-Holtzman, R. and I. Schechter (Biochim. Biophys. Acta (1995) 1263: 96-98) Presnail, J. K. and M. A. Hoy, (Exp. Appl. Acarol. (1994) 18: 301-308)) and the like.

In many embodiments, the at least one transcriptionally active gene or module encodes a protein that has therapeutic activity for the multicellular organism, where such proteins include, but are not limited to: factor VIII, factor IX, ( 1-globin, low-density lipoprotein receptor, adenosine deaminase, purine nucleoside phosphorylase, sphingomyelinase, glucocerebrosidase, cystic fibrosis transmembrane conductance regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides etc, and the like. The above list of proteins refers to mammalian proteins, and in many embodiments human proteins, where the nucleotide and amino acid sequences of the above proteins are generally known to those of skill in the art.

In certain embodiments, the vector also includes at least one transcriptionally active gene or expression module that functions as a selectable marker. A variety of different genes have been employed as selectable markers, and the particular gene employed in the subject vectors as a selectable marker is chosen primarily as a matter of convenience. Known selectable marker genes include: the thymidine kinase gene, the dihydrofolate reductase gene, the xanthine-guanine phosphoribosyl transferase gene, CAD, the adenosine deaminase gene, the asparagine synthetase gene, the antibiotic resistance genes, e.g., $neo^r$ (aminoglycoside phosphotransferase genes), the hygromycin B phosphotransferase gene, genes whose expression provides for the presence of a detectable product, either directly or indirectly, e.g. β-galactosidase, GFP, and the like.

An important feature of the subject minicircle vectors employed in the subject methods is that they do not include bacterial plasmid sequences that would cause the vector to provide only transient, as opposed to persistent, expression. Expression is considered to be transient if expression is not persistent according to the guidelines provided above. Bacterial sequences that are to be excluded from the subject vectors can readily be determined by those of skill in the art using the evaluation assays provided in the Experimental section, below.

A feature of certain embodiments of the subject invention is that the vectors further include a product hybrid sequence of a unidirectional site-specific recombinase. This product hybrid sequence is the result of a unidirectional site specific recombinase mediated recombination of two recombinase substrate sequences, e.g., attB and attP substrate sequences as they are known in the art, and may be either the attR or attL product hybrid sequence. Typically, the product hybrid sequence ranges in length from about 10 to about 500 bp. In certain embodiments, the product sequence is a product hybrid sequence of a unidirectional site specific recombinase that is an integrase, where integrases of interest include, but are not limited to: wild-type phage integrases or mutants thereof, where specific representative integrases of interest include, but are not limited to: the integrases of ΦC31, R4, TP901-1, A118, ΦFC1 and the like.

The overall length of the subject minicircle vectors is sufficient to include the desired elements as described above, but not so long as to prevent or substantially inhibit to an unacceptable level the ability of the vector to enter the target cell upon contact with the cell, e.g., via system administration to the host comprising the cell. As such, the minicircle vector is generally at least about 0.3 kb long, often at least about 1.0 kb long, where the vector may be as long as 10 kb or longer, but in certain embodiments do not exceed this length.

The above-described minicircle vectors may be produced using any convenient protocol. An embodiment of how to construct the vectors employed in the subject methods is provided, infra.

Vector Administration

The subject methods find use in a variety of applications in which it is desired to introduce an exogenous nucleic acid sequence into a target cell, and are particularly of interest where it is desired to express a protein encoded by an expression cassette in a target cell. As mentioned above, the subject vectors may be administered by in vitro or in vivo protocols.

As indicated above, the subject vectors can be used with a variety of target cells, where target cells in many embodiments are non-bacterial target cells, and often eukaryotic target cells, including, but not limited to, plant and animal target cells, e.g., insect cells, vertebrate cells, particularly avian cells, e.g., chicken cells, fish, amphibian and reptile cells, mammalian cells, including murine, porcine, ovine, equine, rat, ungulates, dog, cat, monkey, and human cells, and the like.

In the methods of the subject invention, the vector is introduced into the target cell. Any convenient protocol may be employed, where the protocol may provide for in vitro or in vivo introduction of the vector into the target cell, depending on the location of the target cell. For example, where the target cell is an isolated cell, the vector may be introduced directly into the cell under cell culture conditions permissive of viability of the target cell, e.g., by using standard transformation techniques. Such techniques include, but are not necessarily limited to: viral infection, transformation, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

Alternatively, where the target cell or cells are part of a multicellular organism, the targeting vector may be administered to the organism or host in a manner such that the targeting construct is able to enter the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body. Methods for the administration of nucleic acid constructs are well known in the art. Nucleic acid constructs can be delivered with cationic lipids (Goddard, et al, Gene Therapy, 4:1231-1236, 1997; Gorman, et al, Gene Therapy 4:983-992, 1997; Chadwick, et al, Gene Therapy 4:937-942, 1997; Gokhale, et al, Gene Therapy 4:1289-1299, 1997; Gao, and Huang, Gene Therapy 2:710-722, 1995,), using viral vectors (Monahan, et al, Gene Therapy 4:40-49, 1997; Onodera, et al, Blood 91:30-36, 1998,), by uptake of "naked DNA", and the like. Techniques well known in the art for the transformation of cells (see discussion above) can be used for the ex vivo administration of nucleic acid constructs. The exact formulation, route of administration and dosage can be chosen empirically. (See e.g. Fingl et al., 1975, in "The Pharmacological Basis of Therapeutics", Ch. 1 µl).

The route of administration of the vector to the multicellular organism depends on several parameters, including: the nature of the vectors that carry the system components, the nature of the delivery vehicle, the nature of the multicellular organism, and the like, where a common feature of the mode of administration is that it provides for in vivo delivery of the vector components to the target cell(s) via a systemic route. Of particular interest as systemic routes are vascular routes, by which the vector is introduced into the vascular system of the host, e.g., an artery or vein, where intravenous routes of administration are of particular interest in many embodiments.

Any suitable delivery vehicle may be employed, where the delivery vehicle is typically a pharmaceutical preparation that includes an effective amount of the vector is present in a pharmaceutically acceptable carrier, diluent and/or adjuvant. In certain embodiments, the vector is administered in an aqueous delivery vehicle, e.g., a saline solution. As such, in many embodiments, the vector is administered intravascularly, e.g., intraarterially or intravenously, employing an aqueous based delivery vehicle, e.g., a saline solution.

In many embodiments, the vector is administered to the multicellular organism in an in vivo manner such that it is introduced into a target cell of the multicellular organism under conditions sufficient for expression of the nucleic acid present on the vector to occur. A feature of the subject methods is that they result in persistent expression of the nucleic acid present thereon, as opposed to transient expression, as indicated above. By persistent expression is meant that the expression of nucleic acid at a detectable level persists for an extended period of time, if not indefinitely, following administration of the subject vector. By extended period of time is meant at least 1 week, usually at least 2 months and more usually at least 6 months. By detectable level is meant that the expression of the nucleic acid is at a level such that one can detect the encoded protein in the mammal, e.g., in the serum of the mammal, at a level of at detectable levels at a therapeutic concentration. See e.g., the experimental section, supra. As compared to a control in which a pBluescript vector is employed, protein expression persists for a period of time that is at least about 2 fold, usually at least about 5 fold and more usually at least about 10 fold longer following the subject methods as compared to a control.

A feature of many embodiments of the subject methods is that the above-described persistent expression is achieved without integration of the vector DNA into the target cell genome of the host. As such, the vector DNA introduced into the target cells does not integrate into, i.e., insert into, the target cell genome, i.e., one or more chromosomes of the target cell. In other words, the vector DNA introduced by the subject methods does not fuse with or become covalently attached to chromosomes present in the target cell into which it is introduced by the subject methods. Accordingly, the vectors are maintained episomally, such that they are episomal vectors that provide for persistent expression.

The particular dosage of vector that is administered to the multicellular organism in the subject methods varies depending on the nature of vector, the nature of the expression module and gene, the nature of the delivery vehicle and the like. Dosages can readily be determined empirically by those of skill in the art. For example, in mice where the vectors are intravenously administered in a saline solution vehicle, the amount of vector that is administered in many embodiments typically ranges from about 2 to 100 and usually from about 10 to 50 µg/mouse. The subject methods may be used to introduce nucleic acids of various sizes into the a target cell. Generally, the size of DNA that is inserted into a target cell using the subject methods ranges from about 1 to 12 kb, usually from about 3 to 10 kb, and sometimes from about 4 to 8 kb.

In in vivo protocols, the subject methods may be employed to introduce a nucleic acid into a variety of different target cells. Target cells of interest include, but are not limited to: muscle, brain, endothelium, hepatic, and the like. Of particular interest in many embodiments is the use of the subject methods to introduce a nucleic acid into at least a hepatic cell of the host.

Utility

The subject methods find use in a variety of applications in which the introduction of a nucleic acid into a target cell is desired. Applications in which the subject vectors and methods find use include: research applications, polypeptide synthesis applications and therapeutic applications. Each of these representative categories of applications is described separately below in greater detail.

Research Applications

Examples of research applications in which the subject methods of nucleic acid introduction find use include applications designed to characterize a particular gene. In such applications, the subject vector is employed to introduce and express a gene of interest in a target cell and the resultant effect of the inserted gene on the cell's phenotype is observed. In this manner, information about the gene's activity and the nature of the product encoded thereby can be deduced. One can also employ the subject methods to produce models in which overexpression and/or misexpression of a gene of interest is produced in a cell and the effects of this mutant expression pattern are observed.

Polypeptide Synthesis Applications

In addition to the above research applications, the subject methods also find use in the synthesis of polypeptides, e.g. proteins of interest. In such applications, a minimal plasmid vector that includes a gene encoding the polypeptide of interest in combination with requisite and/or desired expression regulatory sequences, e.g. promoters, etc., (i.e. an expression module) is introduced into the target cell, via in vivo administration to the multicellular organism in which the target cell resides, that is to serve as an expression host for expression of the polypeptide. Following in vivo administration, the multicellular organism, and targeted host cell present therein, is then maintained under conditions sufficient for expression of the integrated gene. The expressed protein is then harvested, and purified where desired, using any convenient protocol.

As such, the subject methods provide a means for at least enhancing the amount of a protein of interest in a multicellular organism. The term 'at least enhance' includes situations where the methods are employed to increase the amount of a protein in a multicellular organism where a certain initial amount of protein is present prior to in vivo administration of the vector. The term 'at least enhance' also includes those situations in which the multicellular organism includes substantially none of the protein prior to administration of the vector. By "at least enhance" is meant that the amount of the particular protein present in the host is increased by at least about 2 fold, usually by at least about 5 fold and more usually by at least about 10 fold. As the subject methods find use in at least enhancing the amount of a protein present in a multicellular organism, they find use in a variety of different applications, including agricultural applications, pharmaceutical preparation applications, and the like, as well as therapeutic applications, described in greater detail infra.

Therapeutic Applications

The subject methods also find use in therapeutic applications, in which the vectors are employed to introduce a therapeutic nucleic acid, e.g., gene, into a target cell, i.e., in gene therapy applications, to provide for persistent expression of the product encoded by the nucleic acid present on the vector. The subject vectors may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VIII, factor IX, β-globin, low-density lipoprotein receptor, adenosine deaminase, purine nucleoside phosphorylase, sphingomyelinase, glucocerebrosidase, cystic fibrosis transmembrane conductor regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, and the like, where the particular coding sequence of the above proteins that is employed will generally be the coding sequence that is found naturally in the host being treated, i.e., human coding sequences are employed to treat human hosts. Cancer therapeutic is genes that may be delivered via the subject methods include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like.

The subject methods also find use in the expression of RNA products, e.g., antisense RNA, ribozymes etc., as described in Lieber et al., "Elimination of hepatitis C virus RNA in infected human hepatocytes by adenovirus-mediated expression of ribozymes," J. Virol. (1996 December) 70(12):8782-91; Lieber et al., "Related Articles Adenovirus-mediated expression of ribozymes in mice," J. Virol. (1996 May) 70(5): 3153-8; Tang et al., "Intravenous angiotensinogen antisense in AAV-based vector decreases hypertension," Am J. Physiol. (1999 December) 277(6 Pt 2):H2392-9; Horster et al. "Recombinant AAV-2 harboring gfp-antisense/ribozyme fusion sequences monitor transduction, gene expression, and show anti-HIV-1 efficacy, Gene Ther. (1999 July) 6(7):1231-8; and Phillips et al., "Prolonged reduction of high blood pressure with an in vivo, nonpathogenic, adeno-associated viral vector delivery of AT1-R mRNA antisense," Hypertension. (1997 January) 29(1 Pt 2):374-80. As such, the subject methods can be used to deliver therapeutic RNA molecules, e.g., antisense, ribozyme, etc., into target cells of the host.

An important feature of the subject methods, as described supra, is that the subject methods may be used for in vivo gene therapy applications. By in vivo gene therapy applications is meant that the target cell or cells in which expression of the therapeutic gene is desired are not removed from the host prior to contact with the vector system. In contrast, the subject vectors are administered directly to the multicellular organism and are taken up by the target cells, following which expression of the gene in the target cell occurs. Another important feature is that the resultant expression is persistent and occurs without integration of the vector DNA into the target cell genome.

Kits

Also provided by the subject invention are kits for use in practicing the subject methods of nucleic acid delivery to target cells. The subject kits generally include the minicircle vector, which vector may be present in an aqueous medium. The subject kits may further include an aqueous delivery vehicle, e.g. a buffered saline solution, etc. In addition, the kits may include one or more restriction endonucleases for use in transferring a nucleic acid into the vector. In the subject kits, the above components may be combined into a single aqueous composition for delivery into the host or separate as different or disparate compositions, e.g., in separate containers. Optionally, the kit may further include a vascular delivery means for delivering the aqueous composition to the host, e.g. a syringe etc., where the delivery means may or may not be pre-loaded with the aqueous composition.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g. a piece or pieces of paper on which the information is printed, in the packaging of the kit, in a package insert, etc. Yet another means would be a computer readable medium, e.g. diskette, CD, etc., on which the information has been recorded. Yet another means that may be present is a website address which may be used via the internet to access the information at a removed site. Any convenient means may be present in the kits.

Methods of Minicircle Vector Production

As summarized above, also provided is a highly efficient method for producing the subject minicircle vectors, as described above. In producing minicircle vectors according to this particular method embodiment, a parent nucleic that includes an expression cassette of interest flanked by attB and attP sites of a unidirectional site specific recombinase is contacted with the unidirectional site specific recombinase that recognizes the flanking attB and attP sites under conditions sufficient for the unidirectional site specific recombinase to mediate a recombination event that produces a minicircle vector from the parent nucleic acid, as described above. By "flanked" is meant that the expression cassette (or other sequence of interest that is to be present in the product minicircle vector, has an att site, e.g., attB and attP, at either end, such that the parent nucleic acid is described by the formula:

-att(P or B)-expression cassette-att(P or B)-

The order of the att sites does not generally matter. The att sites are substrate sites for the unidirectioinal site specific recombinase, and are typically referred to as attB or attP sites by those of skill in the art. Sites of interest include, but are not limited to, the att sites recognized by the specific integrase recombinases above, as well as mutants thereof.

The parent nucleic acid may be present as a variety of different forms, depending at least in part on whether the production method is an in vitro or in vivo method. As such, the parent nucleic acid may be a linear double stranded nucleic acid, a closed circular nucleic acid (such as a bacterial plasmid suitable for use in replication), integrated into genomic DNA, and the like.

As indicated above, the above method may be practiced in vitro or in vivo, e.g., inside of a cell. Where the above method is practiced in vitro, all necessary reagents, e.g., parent nucleic acid, site specific integrase, etc., are combined into a reaction mixture and maintained under sufficient conditions for a sufficient period of time for the site specific recombinase mediated production of the desired product minicircle vectors to occur. Typically, for in vitro reactions, the reaction mixture is maintained at a temperature of between about 20 and 40° C.

In certain embodiments, the above method is an in vitro method in that the recombinase mediated production of the desired product minicircle vector occurs inside of a cell in culture. Examples of such embodiments includes those embodiments where the parent nucleic acid is a plasmid that replicated in a bacterial host to produce large copy numbers of the parent nucleic acid prior to the recombinase mediated vector production step.

In the above in vivo embodiments, the first step may generally be to first prepare a host cell that includes large numbers of the parent nucleic acid. This may conveniently be done by transforming a host cell, e.g., *E. coli.*, with a plasmid that will serve as the parent nucleic acid. The resultant transformed host cell is then maintained under conditions sufficient for the host cell to produce large copy numbers of the parent nucleic acid, as described above.

Upon provision of the host cell having sufficient copy numbers of the parent nucleic acid (e.g., plasmid), the unidirectional site-specific recombinase activity (i.e., that mediates production of the desired vector from the parent nucleic acid) is then produced in the host cell. The desired recombinase activity may be produced in the cell using any convenient protocol. In certain embodiments, the recombinase or a nucleic acid coding sequence therefore may be introduced into the host cell, e.g., as described above. Alternatively, the coding sequence for the recombinase may already be present in the host cell but not expressed, e.g., because it is under the control of an inducible promoter. In these embodiments, the inducible coding sequence may be present on the parent nucleic acid, present on another episomal nucleic acid, or even integrated into the host's genomic DNA. Representative inducible promoters of interest that may be operationally linked to the recombinase coding sequence include, but are not limited to: aracBAD promoter, the lambda pL promoter, and the like. In these embodiments, the step of providing the desired recombinase activity in the host cell includes inducing the inducible promoter to cause expression of the desired recombinase.

Following production of the desired recombinase activity in the host cell, the resultant host cell is then maintained under conditions and for a period of time sufficient for the recombinase activity to mediate production of the desired minicircle vectors from the parent nucleic acids. Typically, the host cell is maintained at a temperature of between about 20 and 40° C.

Following recombinase mediated production of the minicircle vectors from the parent nucleic acids, as described above, the product minicircles may then be separated from the remainder of their "synthesis" environment (e.g., reaction mixture, host cell, etc.) as desired. Any convenient protocol for separating the product minicircles may be employed. Representative protocols are described in the experimental section below.

To assist in distinguishing/separating the desired product minicircle vectors from the byproduct circular remainder of the parent nucleic acid, the byproduct may be selectively cleaved to linearize the byproduct. To provide for this selectable cleavage, a restriction site, e.g., IScel or other suitable site, may be provided in the parent nucleic acid that, following the recombinase mediated recombination event, is present in the byproduct, where the restriction site is then cleaved by its restriction endonuclease, which is provided in the reaction mixture or cell following production of the minicircles and parent byproduct. As with the provision of the recombinase activity, described above, the restriction endonuclease activity may be provided at the appropriate time by a number of different protocols, e.g., by introducing the endonuclease or coding sequence therefor into the reaction mixture/cell following production of the parent byproduct, or inducing expression of the endonuclease to coding sequence that is already present but not expressed in the reaction mixture or cell because it is under the control of an inducible promoter, such as that described above. In these embodiments in which the vector production occurs in a cell, the endonuclease is typically an endonuclease that is not endogenous to the host cell, where representative restriction endonucleases of interest include, but are not limited is to: IScel, I-Ceu I, PI-Psp I and the like.

Also provided are systems for use in practicing the above-described methods of minicircle vector production. The subject systems typically at least include a parent nucleic or precursor thereof, e.g., a nucleic acid having att sites flanking a cloning site, and a host cell. In certain embodiments, the parent nucleic acid further includes a coding sequence for a unidirectional site-specific recombinase that recognizes the att sites, e.g., under the control of an inducible promoter, and/or a coding sequence for restriction endonuclease for cleaving a parent byproduct, e.g., under the control of an inducible promoter. In these embodiments, the system may also include an inducing agent, depending on the nature of the inducible promoter. In yet other embodiments, the system may further include a separate source of the recombinase and/or restriction endonuclease, as described above.

Also provided are kits for use in practicing the subject methods, where the kits may include one or more of the above components of the systems, e.g., parent nucleic acid, host cell, inducing agent, and the like. In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g. a piece or pieces of paper on which the information is printed, in the packaging of the kit, in a package insert, etc. Yet another means would be a computer readable medium, e.g. diskette, CD, etc., on which the information has been recorded. Yet another means that may be present is a website address which may be used via the internet to access the information at a removed site. Any convenient means may be present in the kits.

The following examples are offered by way of illustration and not by way of limitation.

EXPERIMENTAL

I. Materials and Methods

A. Vector construction: To prepare the hAAT minicircle construct pBAD.øC31.RHB (FIG. 1a), we amplified 0031 integrase from the plasmid pCMV.øC31 (Groth, A. C., Olivares, E. C., Thyagarajan, B. & Calos, M. P. A phage integrase directs efficient site-specific integration in human cells. *Proc Natl Aced Sci U S A* 97, 5995-6000. (2000)), using the following primers: 5'-CCG TCC ATG GAC ACG TAC GCG GGT GCT (SEQ ID NO:01), and 5'-ATG CGC GAG CTC GGT GTC TCG CTA CGC CGC TAC (SEQ ID NO:02), and inserted the PCR product into Nco I and Sac I sites of pBAD/Myc-His (Invitrogen, Carlsbad, Calif.), resulting in an intermediate plasmid pBAD.øC31. We composed attB, and attP using the corresponding DNA oligonucleotides (Groth et al., supra), and inserted them into the Spe I and Kpn I sites, respectively, to flank the hAAT expression cassette of the plamsid pRSV.hAAT.bpA (FIG. 2a). The attB, and attP binding sites and expression cassette was inserted into Sac I and Kpn I sites of pBAD.øC31, resulting in pBAD.øC31.RHB. We prepared the vector pBAD.øC31.sApoE.hFIX (FIG. 1b) to produce minicircle expressing hFIX by inserting the expression cassette, derived from pBS.sApoE.HCR.hAAT.hFIX+IntA.bpA (Chen, Z. Y. et al. Linear DNAs concatemerize in vivo and result in sustained transgene expression in mouse liver. *Mol Ther* 3, 403-410. (2001); Miao, C. H. et al. Inclusion of the hepatic locus control region, an intron, and untranslated region increases and stabilizes hepatic factor IX gene expression in vivo but not in vitro. *Mol Ther* 1, 522-532 (2000); and Miao, C. H., Thompson, A. R., Loeb, K. & Ye, X. Long-term and therapeutic-level hepatic gene expression of human factor IX after naked plasmid transfer in vivo. *Mol Ther* 3, 947-957. (2001)), into the Spe I site of pBAD.øC31.RHB after the expression cassette was removed by Xho I digestion.

B. Production of minicircles: We used minicircle producing vectors to transform *E. coli* Top 10 (Invitrogen, Calsbad, Calif.). The bacteria was grown using a New Brunswick Scientific incubator (Model C24, Edison, N.J.). We obtained L-(+)-arabinose from Sigma Chemical Co. (St. Lois, Mo.). We quantified the DNA bands after agarose electrophoresis using Quant One of Bio-Red Laboratories (Hercules, Calif.). We prepared purified expression cassette and 2-fragment DNA from plasmid pRSV.hAAT.bpA as described previously (Chen et al., supra). We dialyzed all the DNA preparations against TE overnight before delivery to animals.

C. Determination of transgene expression in mice: We obtained 6-8 week old C57BU6 mice from Jackson Laboratory (Bar Harbor, Me.). We delivered DNA to mouse livers using a hydrodynamic technique (Zhang, G., Budker, V. & Wolff, J. A. High levels of foreign gene expression in hepatocytes after tail vein injections of naked plasmid DNA. *Hum Gene Ther* 10, 1735-1737 (1999); Liu, F., Song, Y. & Liu, D. Hydrodynamics-based transformation in animals by systemic administration of plasmid DNA. *Gene Ther* 6, 1258-1266 (1999)). We collected mouse blood periodically using a retro-orbital procedure, and determined serum hAAT and hFIX by ELISA as described earlier (Yant, S. R. et al. Somatic integration and long-term transgene expression in normal and haemophilic mice using a DNA transposon system. *Nat Genet.* 25, 35-41. (2000)). All animals were treated under the NIH and Stanford University Animal Care Guidelines.

D. Southern blot analysis of vector DNA structure in mouse livers: We prepared liver DNA using a salt out procedure. Twenty µg of liver DNA from mice receiving one of the four forms of vector DNA expressing hAAT was digested with Bgl II, which did not cut the vector, or Hind III, which cut once through the expression to cassette. We separated the restricted DNAs by electrophoresis in a 0.8% agarose gel, and blotted it onto a nitrocellular membrane. Vector DNA was detected after hybridization with a p32-dCTP-labelled hAAT cDNA probe, and autoradiography or Phosphoimager.

II. Results

A. Production of Minicircles

We constructed the plasmids pBAD.øC31.RHB (FIG. 1a) and pBAD.øC31.hFIX (FIG. 1b) as precursors to the production of minicircular vectors expressing human α1-antitrypsin (hAAT), and human factor IX (hFIX), respectively.

To determine the optimal conditions for induction of øC31 integrase-mediated recombination, an overnight culture ($OD_{600}$~2.50) obtained from a single colony of transformed cells containing pBAD.øC31.RHB was prepared. We determined that the optimal incubation temperature was 32° C., with 1% inducer L-(+)-arabinose added to the bacterial culture (data not shown). However, we found that the recombination efficiency was poor when induction was carried out by adding L-(+)-arabinose to the overnight bacterial growth (FIGS. 1c, and 1d). The recombination efficiency was greatly enhanced by re-suspending the bacteria in fresh LB broth before adding L-(+)-arabinose. Moreover, a slightly better yield of minicircle was obtained when the bacterial culture was re-suspended at a 4 to 1 ratio of overnight growth volume vs fresh LB volume compared with a 1 to 1 ratio (FIGS. 1c and 1d). The optimal conditions for minicircle production include resuspending the overnight bacterial growth 4:1 in fresh LB broth containing 1% L-(+)-arabinose, and incubating the bacteria at 32° C. with shaking at 250 rpm for 60 to 120 minutes. Because the minicircle was about a quarter of the size of the parent vector pBAD.øC31.RHB, we estimated that under these culture conditions, the efficiency of recombination was greater than 97 percent (FIG. 1d).

We purified recombined DNAs from bacteria growth using Qiagen plasmid DNA Kit, and purified minicircles by standard gradient CsCl banding procedure (Sambrook, J., Fritsch, E. F. & Maniatis, T. (eds.). *Molecular cloning: a laboratory manual*, (Cold Spring Harbor Laboratory, New York, 1989)) after linearizing the bacteria backbone circle with Nco I digestion. We obtained about 1 to 1.5 mg of recombined DNA before CsCl purification and 150 to 200 µg of purified minicircle from is 1,000 ml of bacteria growth with minicircle-producing vector pBAD.øC31.RHB, or pBAD.øC31.hFIX.

B. Minicircle-Mediated Transgene Expression In Vivo

To determine if the hAAT-expressing minicircle was devoid of bacterial DNA silencing in vivo, we compared the expression profiles of this minicircular DNA with equal molar amounts of un-recombined plasmid pRSV.hAAT.bpA (FIG. 2a), a linear DNA mixture of expression cassette and bacterial backbone, or equal molar amounts of purified linear expression cassette containing the same DNA sequence as the minicircle except for the 37 bp attR hybrid site after transformation into mouse liver.

Consistent with our previous observation (Chen et al., manuscript submitted), serum concentrations of hAAT obtained from mice injected with purified expression cassette was more than 3-fold higher than that of mice received 2-fragment DNA, and 20- to 43-fold higher than ccDNA injected mice (FIG. 2b, left panel) 3 weeks after DNA infusion. The mice receiving minicircle DNA produced 10- to 13-fold more serum hAAT than those receiving the purified expression cassette, which was 200- to 560-fold higher than that of ccDNA group. Mice receiving ccDNA also expressed a high level of serum hAAT initially, but the serum reporter level dropped by 710-fold in the first 3 weeks, and continued to decrease afterward. Our data clearly demonstrate that the minicircle was the most efficient vector form and could express persistent and high levels of transgene product.

To demonstrate the potential for therapeutic efficacy, we compared the hFIX expressing minicircle to the corresponding un-recombined plasmid. Animals infused with this minicircle expressed a high level of serum hFIX which stabilized at about 12 microgram hFIX per ml of serum (more than twice normal) for up to 7 weeks (length of experiment. FIG. 2b, right panel). High levels of serum hFIX were obtained in mice receiving the un-recombined plasmid one day after DNA infusion, but the serum therapeutic protein dropped more than 45-fold in 3 weeks and continued to decrease afterward.

C. Southern Blot Analysis of Minicircle DNA in Mouse Livers

Figure 3B:
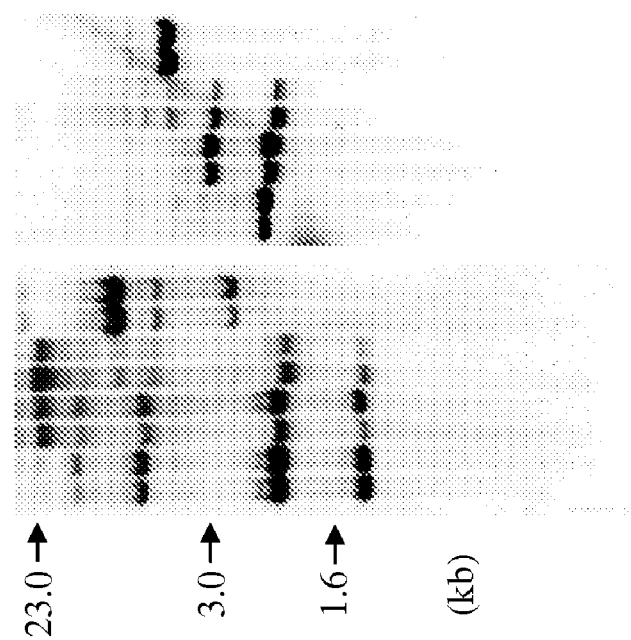
FIGS. 3a to 3b. Southern blot analysis of vector DNA in mouse livers. Liver DNA from mice treated as indicated in the legend of FIG. 2b left panel.
Figure 3A:
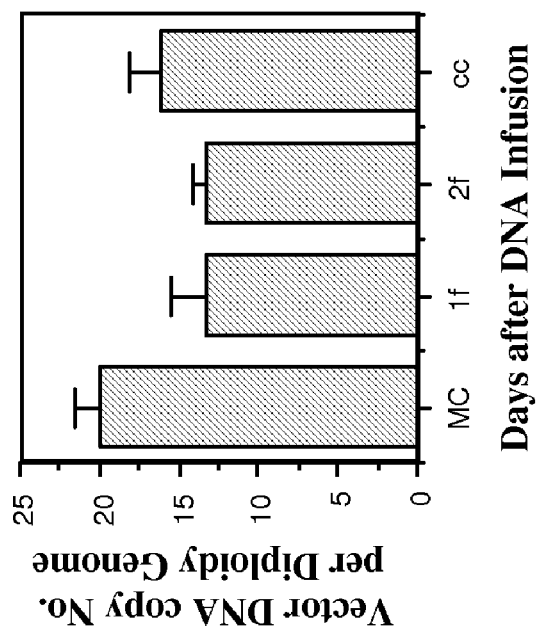

Although in previous studies, we found no difference in the amount of DNA after infusion of ccDNA or linear DNA (Chen et al., supra), we wanted to establish if the same was true in minicircle injected mice. Liver vector DNA copy number was determined in mice receiving different forms of the hAAT vector DNA 15 weeks after injection (FIG. 2b, left panel). About 13 to 20 copies of vector DNA per diploidy mouse genome was detected in each group (FIG. 3a). Consistent with previous observations, our data indicate that difference in serum hAAT levels was not due to variations in the amount of vector DNA in mouse liver.

Previously, we have demonstrated that circular plasmids remained as intact circles in mouse liver (Chen et al., supra) (Chen et al., manuscript submitted). In order to establish if minicircle DNA behaved like other circular plasmids in mouse livers, we analyzed the molecular structure of vector DNA by Southern blot. With Bgl II digestion, which does not cut in the vector, we found multiple bands representing aggregates of supercoiled minicircles. These bands were converted into a single length monomer by digestion with Hind III, which cuts once in the vector (FIG. 3b). Thus, similar to the uncut circular plasmid, the minicircle DNA was maintained as an intact episomal circle in mouse liver. In addition, consistent with our previous observations, the 2 linearized DNAs formed large concatemers, as represented by the 23 kb bands, as well as small circles (FIG. 3b).

III. Discussion

We demonstrate above that large quantities of minicircle DNA vectors devoid of bacterial DNA sequences can be produced by using the phage øC31 integrase-mediated recombination in *E. coli*. The technique is relatively simple, the yield is high, and the production can be easily scaled up. We establish that minicircles can express high and persistent levels of transgene products in mouse liver. Minicircles expressed 45- and 560-fold more serum hFIX and hAAT than their parent unrecombined plasmids in mouse liver. Importantly, and similar to our previous results (Chen et al., supra) (Chen et al., manuscript submitted), this difference in gene expression was not related to changes in the amount of vector DNA in mouse liver. Together, these results further confirm the finding that the bacterial backbone plays an inhibitory role in episomal transgene expression. As compared to the linear purified expression cassette, minicircle DNA expressed more than 10-fold higher levels of serum hAAT, suggesting that the minicircle was an optimal episomal vector form for transgene expression, probably because of its circular configuration. Alternatively, substantial amounts of linear expression cassette might be inactivated via the partial loss of promoter, and/or polyadenylation DNA sequences during the non-homology-end-joining process.

Since the transcriptional silencing effect is overcome by using minicircular DNA, transgene expression will not be lost except during cell division or cell death. It has been hypothesized that when plasmid DNA is delivered within some lipid DNA complexes, a loss of transgene expression occurs due to an immune response against CpG dinucleotides present in bacterial DNA. We have previously established that this is unlikely to occur in our studies because there is no loss of DNA and similar expression profiles are found in normal and immunodeficient mice (Chen et al., supra) (Chen et al., manuscript submitted). It has been well documented that plasmids can undergo nucleation, and persist in an episomal status for months or years not only in liver (Chen et al., supra), but also in heart (Gal, D. et al. Direct myocardial transformation in two animal models. Evaluation of parameters affecting gene expression and percutaneous gene delivery. *Lab Invest* 68, 18-25. (1993)), and skeletal muscle (Wolff, J. A., Ludtke, J. J., Acsadi, G., Williams, P. & Jani, A. Long-term persistence of plasmid DNA and foreign gene expression in mouse muscle. *Hum Mol Genet*. 1, 363-369. (1992)). It is reasonable to expect that persistence of transgene expression from minicircle can also be achieved from these, and other organs, with a low cell turnover rate.

IV. One Step Column Purification of Minicircle DNA Vector from Bacteria Growth A. Abstract: The following discussion demonstrations the use of a one-step column purification protocol of minicircle DNA vector from bacterial growth that produces about 1 mg of minicircle DNA vector with more than 96% purity from 1,000 ml of bacterial growth using Qiagen DNA Kit without additional work. The following protocol enables production of large quantity of minicircle vector for clinical use.

Figure 4A:
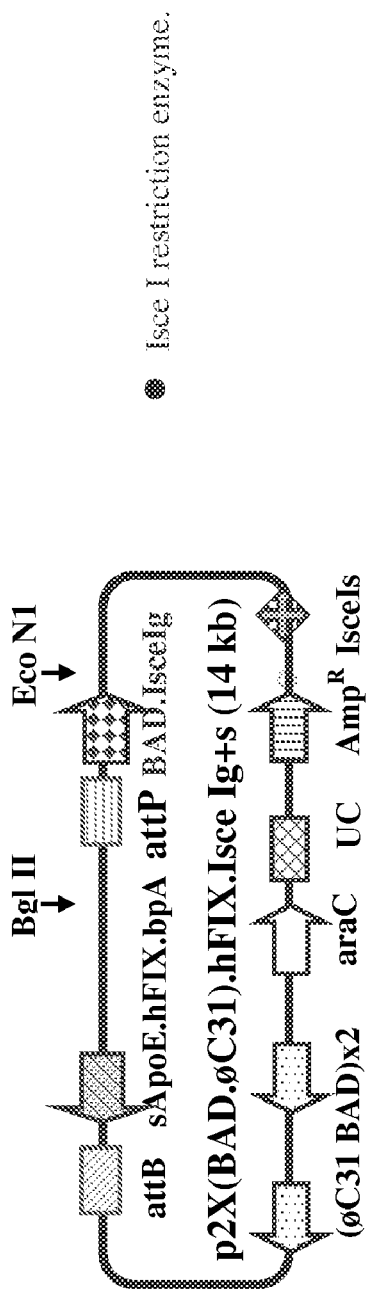
FIGS. 4a to 4c provide a schematic representation of a second representative minicircle vector preparation protocol.

B. Plasmid construct: FIG. 4a schematically illustrates the minicircle producing construct p2xBAD.øC31.hFIX.Isce Ig$^+$s for this study. Two copies of the integrase øC31 gene, and one copy of the restriction enzyme Isce I gene are all placed under the control of araC/BAD promoter. The expression cassette sApoE.hFIX.bpA flanked with attB and attP, and an I-Sce I restriction site (I-Sce Is) are included in the same construct. The plasmid backbone is pUC19 containing a pUC DNA replication origin (UC), and an ampicillin resistance gene (Amp$^R$).

C. Preparation of minicircle: The plasmid p2X(BAD.øC31).hFIX.Isce Ig+s (FIG. 4a) was used to transform Top 10 bacteria. A colony of the transformed bacteria was grown overnight in 200 ml of LB broth with 10 mg/ml of ampicillin using a standard bacteria growth procedure. The bacteria was further grown overnight in 1500 ml of LB/ampicillin broth. The bacteria was spun down, re-suspended 4 to 1 in fresh LB broth containing 1% of L-arabinose, incubated at 32° C. with constant shaking at 250 rpm for one hour as described above. One half of the bacteria were then incubated continuously at 32° C. for additional two hours, while another half were incubated at 37° C. for 2 hours. The bacteria was spun down, and processed for plasmid DNA preparation using Qiagen kit.

Figure 4C:
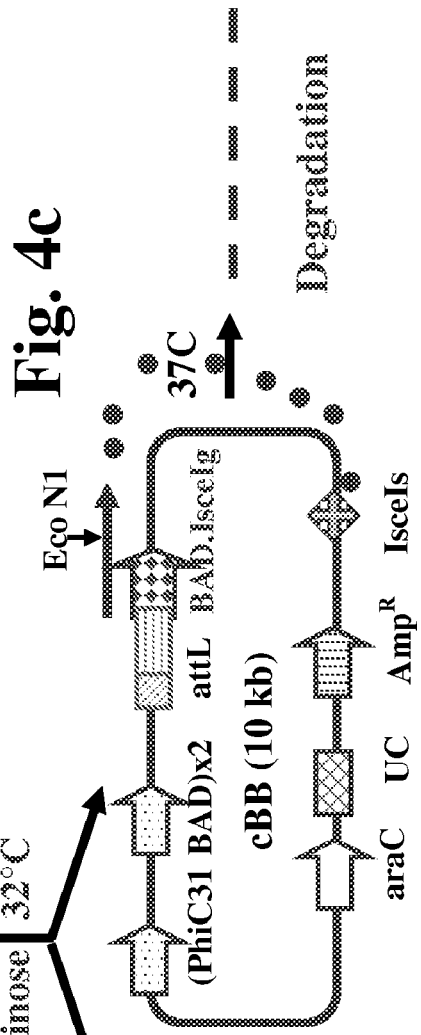
Figure 4B:
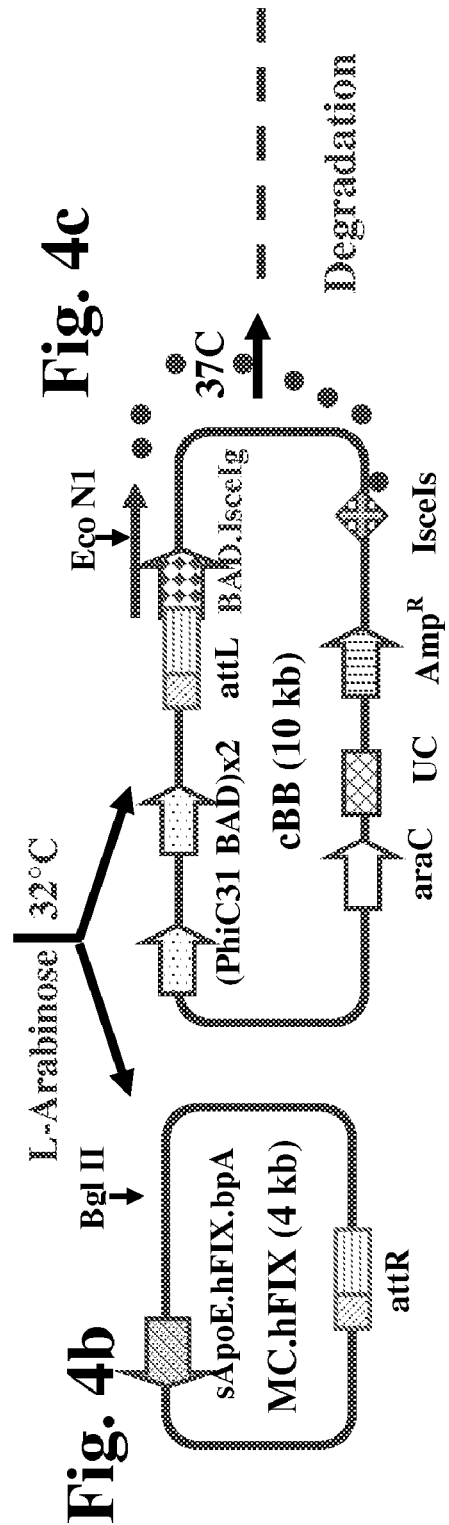

FIG. 5 demonstrates the purity of the minicircle vector DNA. 0.8 µg of DNA each was digested with Bg III and Eco N1, each of them cuts once through the expression cassette or the bacterial backbone, respectively. The 1.4 kb and 12.3 kb bands in lane 1 were the restriction products of unrecombined plasmid (FIG. 4a), while the 4.1 kb and the band slightly below 12.3 kb in lane 2 and 3 frOrn above-mentioned 2 different recombination-restriction conditions were the linearized minicircle (FIG. 4b) and bacterial DNA (FIG. 4c), respectively.

Quantification of the DNA bands (Quant One of Bio-Rad, Hercules, Calif.) demonstrated that the purity of the minicircle in lane 2 and 3 were 96% and 97% respectively.

D. Discussion: The technology of one step column purification of, minicircle DNA vector from bacteria growth enables large scale production of minicircle for clinical use. This technology saves time and materials so that is more cost-effective. More importantly, it allows production of large quantities of minicircle vector for clinical use without involving any toxic material, such as ethium bromide. In this one step protocol, the I-Sce I gene is included to express the restriction enzyme which linearizes the circular DNA by cutting a built-in I-Sce I restriction site in the minicircle producing construct. The linearized DNA is then degraded by the bacterial nucleases, and the minicircle will become the only episomal DNA to be purified by commercially available kit. Currently, both øC31 and I-Sce I genes are driven by araC-BAD promoter ao that the two enzymes are induced simultaneously upon addition of the inducer L-arabinose. Conse quently, circular bacterial DNA linearization and the øC31-mediated minicircle formation occur at the same time, resulting in a partial loss of unrecombined plasmid and hence a lower yield of minicircle DNA. However, we reason that percent of premature linearization/degradation is limited, because the recombinase øC31 is highly efficient and relatively stable. The øC31 can process the recombination reaction to almost completeness in 30 to 60 minutes. In contrast, the I-Sce I enzyme is unstable with a half-life of only 5 minutes also. The I-Sce I enzyme in the bacteria could not reach a high level. Furthermore, we use 2 copies of the 0031.recombinase is to further speed up the minicircle formation and decrease the premature linearization/degradation further.

The above-described invention is the product of highly unexpected results, observed by the inventors. Specifically, prior to the inventors' work described herein, it was believed, and also observed, that circular vectors, e.g., plasmids, could not provide for persistent high-level protein expression. As reported herein, by removing bacterial sequences from circular vectors, the inventors were unexpectedly able to obtain circular vectors that provide for persistently high levels of protein expression. Based on knowledge of the inventors at the time of filing of the present application, it was not at all obvious that one could achieve persistent high-level expression from circular vectors by removing bacterial silencing sequences from the vectors.

It is evident from the above results and discussion that an improved method of transferring a nucleic acid into a target cell is provided by the subject invention. Specifically, the subject invention provides a highly efficient transgene expression vector which does not employ viral vectors and does not require target cell genome integration and yet provides for persistent high level gene expression and therefore provides many advantages over prior art methods of nucleic acid transfer. Also provided is a highly efficient and readily scalable method for producing the vectors employed in the subject methods. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A circular vector devoid of bacterial transcriptional silencing sequence, said vector comprising:
   a product hybrid sequence of a resolvase integrase and an expression cassette,
   wherein said vector provides for persistent and high level expression when present in a cell.

2. The circular vector according to claim 1, wherein said resolvase integrase is a unidirectional site-specific integrase.

3. The circular vector according to claim 2, wherein said integrase is ΦC31.

4. The circular vector according to claim 1, wherein said vector ranges in length from about 0.3 to about 10 kb.

5. The circular vector according to claim 1, wherein said vector is double stranded.

6. The circular vector according to claim 1, wherein said vector is a deoxyribonucleic acid vector.

7. A kit for introducing an expression cassette into a target cell, said kit comprising:
   (a) a vector according to claim 1; and
   (b) instructions for using said vector for introducing an expression cassette into a target cell.

8. The vector according to claim 1, wherein said resolvase integrase is selected from the group consisting of ΦC31, R4, TP901-1, A118, and ΦFC1.

9. The vector according to claim 1, wherein said vector provides for persistent and high level expression for at least 3 weeks when present in a cell.

10. The vector according to claim 1, wherein said vector provides for persistent and high level expression for at least 28 days when present in a cell.

11. A circular vector devoid of bacterial transcriptional silencing sequence, said vector comprising:
    a product hybrid sequence of a resolvase integrase and an expression cassette,
    wherein said vector provides for persistent and high level expression for at least 3 weeks when present in a cell.

12. The circular vector according to claim 11, wherein said resolvase integrase is a unidirectional site-specific integrase.

13. The vector according to claim 12, wherein said resolvase integrase is selected from the group consisting of ΦC31, R4, TP901-1, A118, and ΦFC1.

14. The circular vector according to claim 13, wherein said integrase is ΦC31.

15. The circular vector according to claim 11, wherein said vector ranges in length from about 0.3 to about 10 kb.

16. The circular vector according to claim 11, wherein said vector is double stranded.

17. The circular vector according to claim 11, wherein said vector is a deoxyribonucleic acid vector.

18. A circular vector devoid of bacterial transcriptional silencing sequence, said vector comprising:
    a product hybrid sequence of a ΦC31 integrase and an expression cassette,
    wherein said vector provides for persistent and high level expression for at least 3 weeks when present in a cell.

19. The circular vector according to claim 18, wherein said vector ranges in length from about 0.3 to about 10 kb.

20. The circular vector according to claim 18, wherein said vector is double stranded.

21. The circular vector according to claim 18, wherein said vector is a deoxyribonucleic acid vector.

\* \* \* \* \*

SEQUENCE LISTING

<160> NUMBER OF SEQ ID NOS: 2

<210> SEQ ID NO 1
<211> LENGTH: 27
<212> TYPE: DNA
<213> ORGANISM: Phi-C31 phage

<400> SEQUENCE: 1
ccgtccatgg acacgtacgc gggtgct    27

<210> SEQ ID NO 2
<211> LENGTH: 33
<212> TYPE: DNA
<213> ORGANISM: Phi-C31 phage

<400> SEQUENCE: 2
atgcgcgagc tcggtgtctc gctacgccgc tac    33